United States Patent [19]

Mimura et al.

[11] Patent Number: 4,775,743
[45] Date of Patent: Oct. 4, 1988

[54] PEPTIDE DERIVATIVES

[75] Inventors: Tsutomu Mimura; Yasuhiro Kohama; Chikara Fukaya, all of Osaka; Masahiro Watanabe, Hyogo; Kazumasa Yokoyama, Osaka, all of Japan

[73] Assignee: Green Cross Corporation, Osaka, Japan

[21] Appl. No.: 905,815

[22] Filed: Sep. 10, 1986

[30] Foreign Application Priority Data

Sep. 10, 1985 [JP] Japan .................. 60-198606

[51] Int. Cl.$^4$ .............................................. C07K 7/06
[52] U.S. Cl. ..................................... 530/330; 514/821
[58] Field of Search ................ 530/329, 330, 331; 548/518; 514/17, 821

[56] References Cited

FOREIGN PATENT DOCUMENTS 787917 6/1968 Canada ........................ 260/998.2
57-16535682 10/1982 Japan .

Primary Examiner—Ronald W. Griffin
Assistant Examiner—Teresa D. Wessendorf
Attorney, Agent, or Firm—Sughrue, Mion, Zinn, Macpeak & Seas

[57] ABSTRACT

New peptide derivatives represented by the following general formula $R_1$-Pro-Hyp-$R_2$ wherein $R_1$ is a hydrophobic radical, $R_2$ is a hydrophilic radical, Pro is prolyl and Hyp is hydroxyprolyl show more powerful inhibitory action against platelet agglutination than conventional drugs and have potential use as anti-agglutination agent. The peptide derivative can be prepared by condensing a peptide containing a hydrophobic radical with a carboxylic acid containing a hydrophilic radical. The peptide derivative can be used in the form of parenteral injections, tablets, capsules or powder, the typical daily dose being in the range from 1 mg to 500 mg for adults.

7 Claims, 2 Drawing Sheets

PEPTIDE DERIVATIVES

BACKGROUND OF THE INVENTION

1. Field of the Invention

This invention relates to new peptides useful as a medicine. This invention also relates to processes for preparing new peptides.

2. Description of the Prior Art

An active peptide, Pro-Hyp-Gly-Ala-Gly, (hereinafter referred to as compound P), is known from Japanese Patent Application (OPI) No. 165356/82 (the term "OPI" as used herein means an "unexamined published application"). This compound has potent anti-arrhythmic and platelet-agglutination preventing activity.

Compound P showed low toxicity and was expected as a remedy against ischemic cardiac insufficiencies. However, its effective dose for oral administration is rather large compared with conventional drugs, and its action does not last long as is apparent from its half-life in the blood as short as about ten minutes. Therefore, improvement has been desired.

SUMMARY OF THE INVENTION

The object of this invention is to provide new peptide derivatives having higher physiological activity, cell membrane permeability, absorption speed and metabolic turnover compared with compound P.

Another object of this invention is to provide processes for producing new peptide derivatives.

As a result of extensive studies it has now been found that these objects can be achieved by production of compounds having a general structure of (Hydrophobic group)-Pro-Hyp-(Hydrophilic group). This invention was accomplished based on these findings.

Thus this invention relates to new peptide derivatives represented by general formula (I)

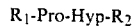  (I)

wherein $R_1$ represents a hydrophobic radical, $R_2$ represents a hydrophilic radical, Pro stands for prolyl and Hyp stands for hydroxyprolyl.

In another aspect, this invention relates to a process for producing new peptide derivatives represented by general formula (I)

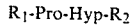  (I)

wherein $R_1$ represents a hydrophobic radical, $R_2$ represents a hydrophilic radical, Pro stands for prolyl and Hyp stands for hydroxyprolyl, by condensing a peptide containing a hydrophobic radical with a carboxylic acid containing a hydrophilic radical.

DETAILED DESCRIPTION OF THE INVENTION

Figure 1:
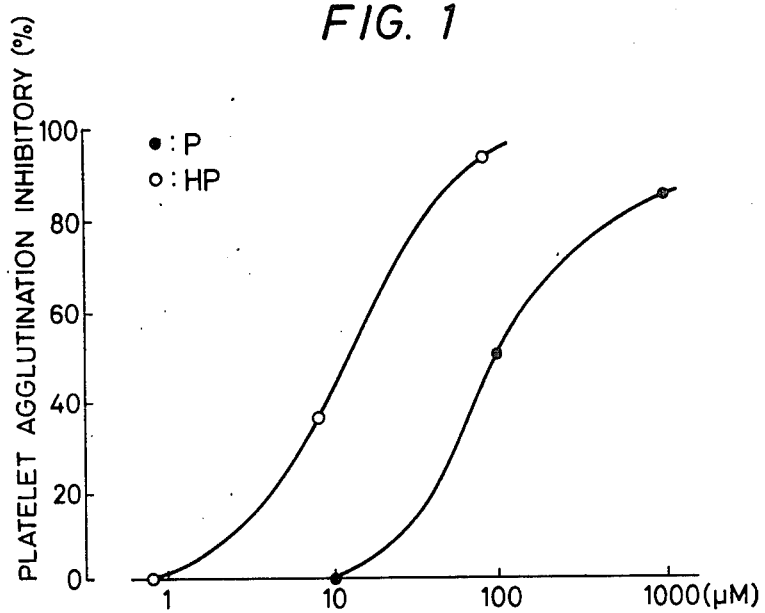
FIG. 1 shows the in vitro inhibitory effects of compound P (control) and compound HP (compound of Example 1) against agglutination of rat PRP (platelet-rich plasma) induced by arachidonic acid.

The hydrophobic radical may be the residue of a hydrophobic amino acid, or linear or branched 1C to 10C alkyl, 6C to 10C aryl, or 7C to 10C aralkyl having a linear or branched alkyl moiety. These hydrophobic radicals may also contain, in the main and/or side chains, keto, carboxyl, hydroxyl, ether, ester, acid amide or amino acid residues.

As typical examples of hydrophobic amino acids there may be mentioned, among others, phenylalanine, tryptophan, leucine and isoleucine. The most preferred hydrophobic radicals are those represented by the following general formula

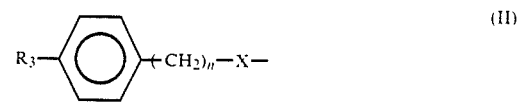  (II)

wherein X represents —CO—, —CH(COOH)— or —CH$_2$—; $R_3$ represents hydrogen or hydroxyl; and n is an integer from 1 to 8, preferably from 1 to 4.

As examples of the hydrophilic radical may be mentioned linear or branched 1C to 16C alkyl, 6C to 16C aryl and 7C to 16C aralkyl having a linear or branched alkyl moiety, containing, at the terminal thereof, carboxyl, sufonic acid, sulfate, amino, quaternary ammonium, phosphate, hydroxyl, acid amide, thiol, nitrile, thiocyanate, nitro or imino group, or halogen atom. In addition, some peptide residues or peptide derivatives may also be used as the hydrophilic radical. In the latter case, suitable peptide is one composed of 2 to 6 amino acids (preferably glycine (Gly) or alanine (Ala)), for example, a peptide represented by formula (III).

Gly-Ala-Gly  (III)

The compounds (I) of this invention can be prepared, for example, by condensing a peptide containing a hydrophobic radical with a carboxylic acid containing a hydrophilic radical.

Of the compounds of formula (I), those in which $R_1$ is the radical represented by formula (II) and $R_2$ is the residue of compound (III), namely, a compound represented by formula

  (IV)

wherein $R_3$, X and n have the same meanings as defined above, can be synthesized by condensing a peptide containing a hydrophilic radical represented by (Pro)$_m$-Hyp-Gly-Ala-Gly  (V)

wherein m is 0 or 1, with a carboxylic acid containing a hydrophobic radical represented by a formula

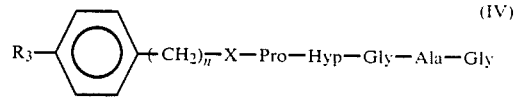  (VI)

wherein Y represents

when n is 1, or

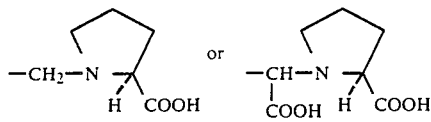

when n is 0.

As the amino-protective group may be used, for example, t-butoxycarbonyl (BOC), benzyloxycarbonyl (hereinafter abbreviated as Z) or tosyl group.

The compound of formula (V) and the compound of formula (VI) each is used in a concentration of preferably from 0.1 to 1.0M, more preferably 0.1 to 0.5M.

Any known condensing agents may be used, but the preferred is a carbodiimide such as N,N′-dicyclohexylcarbodiimide (DCC). The condensing agent is preferably used in an amount of 1 to 3 mol equivalents, more preferably 1.1 to 1.3 mol equivalents.

The proportion of the condensing agent, the compound of formula (V) and the compound of formula (VI) is preferably 1–3/1/1–3, more preferably 1.1–1.3/1/1.1–1.3 by mol equivalent.

Preferable solvents include ethyl acetate, acetonitrile, dichloromethane, chloroform, tetrahydrofuran and N,N-dimethylformamide.

The condensation reaction is preferably carried out at a temperature in the range from $-10°$ to $100°$ C., most preferably in the range from $0°$ to $50°$ C., for 2 to 20 hours.

More particularly, a compound of formula (I) in which $R_1$ is a radical represented by

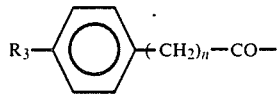

and $R_2$ is the residue of compound (III), namely, a compound of

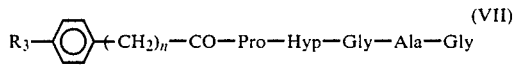
(VII)

can be synthesized by condensation between compound P and a carboxylic acid represented by the formula (VIII)

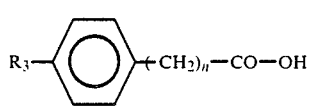
(VIII)

Compound P is a pentapeptide which may be prepared by known methods as detailed below (the liquid phase method and the solid phase method).

A compound of formula (I) in which $R_1$ is a radical represented by

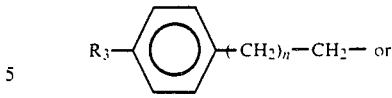

and $R_2$ is the residue of comound (III), namely, a compound represented by formula (IX) or (X)

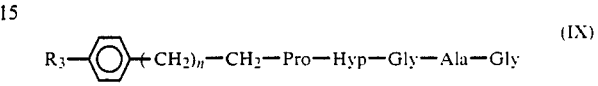
(IX)

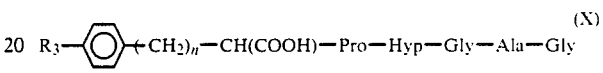
(X)

can be synthesized by reaction of the compound of formula (XI)

Hyp-Gly-Ala-Gly    (XI)

with a compound of formula (XII) or (XIII), respectively.

(XII)

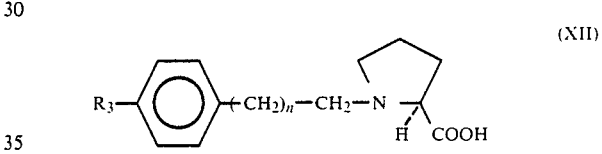

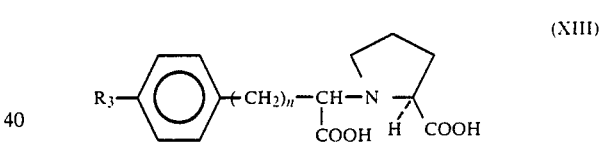
(XIII)

The reaction conditions are the same as described above.

The N-substituted proline derivatives (compounds (XII) and (XIII)) may be easily obtained by reductive amination from proline and a corresponding aldehyde or α-ketocarboxylic acid, as described in Fieser & Fieser, *Reagents for Organic Synthesis*, A Wiley-Interscience Publication, Vol. IV, p. 448–449 (1974).

The compounds of formula (I) thus formed can be isolated and purified by gel filtration, ion-exchange chromatography, high performance liquid chromatography (HPLC) using a reverse column, silica gel chromatography, or by combinations thereof. Either of the solid phase method and the liquid phase method (as described in S. Aonuma et al., *Chem. Pharm. Bull.*, 28. 3332–3339 and 3340–3346 (1980), ibid., 32, 219–227 (1984), *J. Pharm. Dyn.*, 5, 40–48 (1982) and *Yakugaku Zasshi*, 103, 662–666 (1983)) shown below may be used for the synthesis of compound P and compounds of (XI) and (I).

SOLID PHASE METHOD

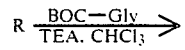

-continued

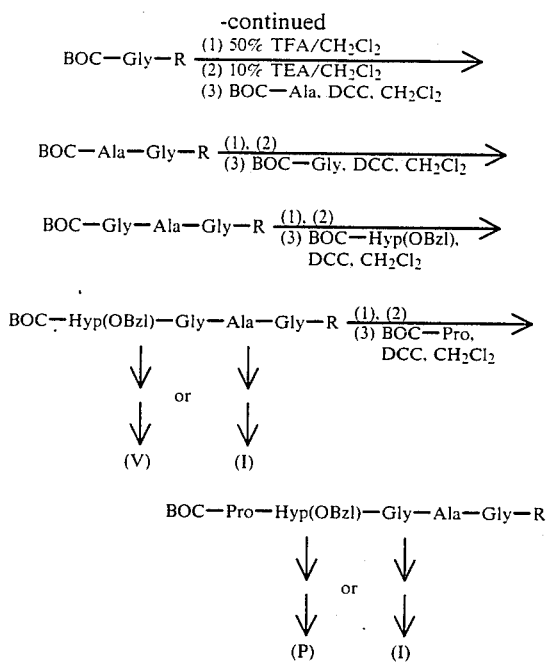

R: Chlorinated resin
DCC: Dicyclohexylcarbodiimide
TEA: Triethylamine,
BOC: tert-Butoxy carbonyl
TFA: Trifluoroacetic acid
Bzl: Benzyl

LIQUID PHASE METHOD

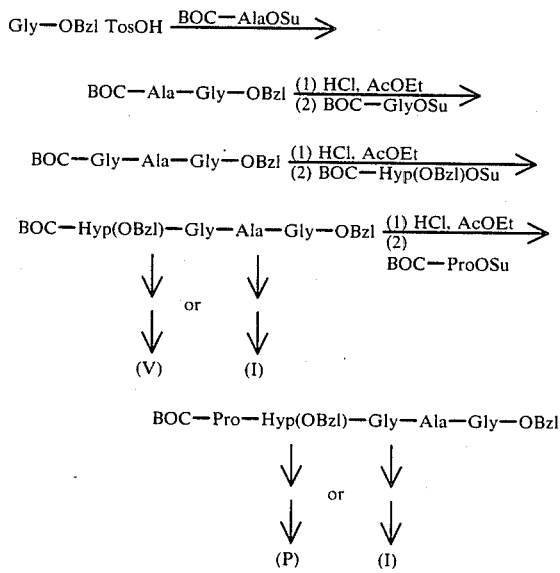

Su: Succinimide
AcOEt: Ethyl acetate
Tos:

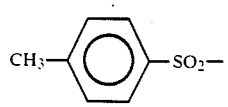

Bzl: Benzyl

In actual practice, it is preferable that compounds (P) and (VIII) are used for the succeeding steps with their protective groups left unreleased, as shown in the Examples given below.

The peptide derivatives of this invention represented by the general formula (I) show more potent inhibitory action against platelet agglutination than conventional drugs and are useful as anti-agglutination agent.

In actual application, said peptide derivatives may be used in the form of parenteral injections, tablets, capsules or powder.

Typical daily dose of said peptide derivatives is in the range from 1 mg to 500 mg for adults.

The following Examples and Test Examples further illustrate this invention but are not intended to limit its scope.

EXAMPLE 1

Synthesis of

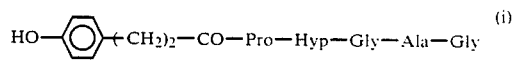

(1) Preparation of N-tert-butyloxycarbonyl-L-alanyl-glycine benzyl ester

To a solution of 12.9 g of glycine benzyl ester tosylate in 200 ml acetonitrile cooled to 0° C., was added dropwise triethylamine (5.3 ml), followed by addition of 12 g of N-tert-butyloxycarbonylalanine N-hydroxysuccinimide ester (prepared by reaction of N-tert-butyloxycarbonylalanine with N-hydroxysuccinimide in the presence of dicyclohexylcarbodiimide). The resulting solution was stirred at 0° C. for one hour and then at room temperature for 18 hours. At the end of reaction, the solvent was distilled off under reduced pressure, the residue was extracted with ethyl acetate, and the extract was washed with 5% acetic acid, water and saturated aqueous solution of sodium chloride in that order, giving 16 g of crude product. Purification of this crude product by silica gel chromatography (chloroform:methanol=40:1) afforded 12.6 g of pure N-tert-butyloxycarbonyl-L-alanyl-glycine benzyl ester.

$^1$H NMR (CDCl$_3$), δ: 1.35 (d, J=7 Hz, 3H), 1.42 (s, 9H), 4.02 (d, J=5 Hz, 2H), 3.95-4.35 (m, 1H), 5.12 (s, 2H), 5.45 (d, J=7 Hz), 7.12 (t, J=6 Hz, 1H), 7.28 (s, 5H).

IR, $\nu_{max}^{KBr}$: 3310, 1738, 1682, 1655 cm$^{-1}$.

(2) Preparation of N-tert-butyloxycarbonyl-glycyl-L-alanyl-glycine benzyl ester

A solution of N-tert-butyloxycarbonyl-L-alanyl-glycine benzyl ester (12.6 g) in 80 ml of anhydrous ethyl acetate was added dropwise over a period of 15 minutes to 130 ml of 4N HCl solution in anhydrous ethyl acetate previously cooled to 0° C., and the mixture was stirred at room temperature for 30 minutes. At the end of reaction, the solvent and excess hydrogen chloride were distilled off under reduced pressure, giving white solid.

This solid was dissolved in 200 ml acetonitrile, the solution was cooled to 0° C., and 5.3 ml of triethylamine was added dropwise to the solution, followed by addition of 11.2 g of N-tert-butyloxycarbonyl-glycine N-hydroxysuccinimide ester (prepared by reaction of N-tert-butyloxycarbonyl-glycine with N-hydroxysuccinimide in the presence of dicyclohexylcarbodiimide). The resulting solution was stirred at 0° C. for 20 minutes and then at room temperature for 18 hours. At the end of reaction, 10 ml of 5% acetic acid was added, the solvent was distilled off under reduced pressure, the residue was extracted with ethyl acetate, and the extract was washed with 1% acetic acid, water and saturated aqueous solution of sodium chloride in that order, given 15 g of crude product. Purification of this crude product by silica gel chromatography (chloroform:methanol=40:1) afforded 10.6 g of pure product.

BOC-Gly-Ala-GlyOBzl $^1$H NMR (DMSO-d$_6$+CDCl$_3$), δ: 1.26 (d, J=7 Hz, 3H), 1.40 (s, 9H), 3.62 (d, J=5 Hz, 2H), 3.90 (d, J=5 Hz, 2H), 4.41 (t, J=7 Hz, 1H), 5.09 (s, 2H), 6.60 (t, J=5 Hz, 1H), 7.30 (s, 5H), 7.79 (d, J=7 Hz, 1H), 8.18 (t, J=5 Hz, 1H).

IR, $\nu_{max}^{KBr}$: 3300, 1745, 1648 cm$^{-1}$.

(3) Preparation of N-tert-butyloxycarbonyl-O-benzyl-L-hydroxyprolyl-glycyl-L-alanyl-glycine benzyl ester A solution of N-tert-butyloxycarbonyl-glycyl-L-alanyl-glycine benzyl ester (9.95 g) in 80 ml of anhydrous ethyl acetate was added dropwise over a period of 15 minutes to 120 ml of 4.3N HCl solution in anhydrous ethyl acetate previously cooled to 0° C., and the mixture was stirred at 0° C. for 10 minutes and then at room temperature for 15 minutes. At the end of reaction, the solvent and excess hydrogen chloride was distilled off under reduced pressure, giving white solid.

This solid was suspended in 200 ml acetonitrile, the suspension was cooled to 6° C., and 3.5 ml of triethylamine was added dropwise to the suspension, followed by addition of 11.6 g of N-tert-butyloxycarbonyl-O-benzyl-L-hydroxyproline N-hydroxysuccinimide ester (prepared by reaction of N-tert-butyloxycarbonyl-O-benzyl-L-hydroxyproline with N-hydroxysuccinimide in the presence of dicyclohexylcarbodiimide). Acetonitrile (100 ml) was further added, and the resulting mixture was stirred at 0° C. for 20 minutes and then at room temperature for 18 hours. At the end of reaction, 10 ml of 5% acetic acid was added, the solvent was distilled off under reduced pressure, the residue was extracted with ethyl acetate, and the extract was washed with 0.1% acetic acid, water and saturated aqueous solution of sodium chloride in that order, giving 17 g of crude product. Purification of this crude product by silica gel chromatography (chloroform:methanol=20:1) afforded 14 g of pure product.

BOC-Hyp(OBzl)-Gly-Ala-GlyOBzl $^1$H NMR (CDCl$_3$), δ: 1.32-1.44 (m, 12H), 2.0-2; 0.5 (m, 2H), 3.4-4.75 (m, 9H), 4.43 (s, 2H), 5.05 (s, 2H), 7.05-7.8 (m, 13H).

IR, $\nu_{max}^{KBr}$: 3290, 1752, 1700, 1665, 1638 cm$^{-1}$.

(4) Preparation of N-tert-butyloxycarbonyl-L-prolyl-O-benzyl-L-hydroxyprolyl-glycyl-L-alanyl-glycine benzyl ester A solution of N-tert-butyloxycarbonyl-O-benzyl-L-hydroxyprolyl-glycyl-L-alanyl-glycine benzyl ester (14.0 g) in 80 ml of anhydrous ethyl acetate was added dropwise over a period of 15 minutes to 100 ml of 5.2N HCl solution in anhydrous ethyl acetate previously cooled to 0° C., and the mixture was stirred at 0° C. for 10 minutes and then at room temperature for 10 minutes. At the end of reaction, the solvent and excess hydrogen chloride were distilled off under reduced pressure, giving white solid.

This solid was suspended in 200 ml acetonitrile, the suspension was cooled to 0° C., and 3.3 ml of triethylamine was added dropwise to the suspension, followed by addition of 8.2 g of N-tert-butyloxycarbonyl-L-proline N-hydroxysuccinimide ester (prepared by reaction of N-tert-butyloxycarbonyl-L-proline with N-hydroxysuccinimide in the presence of dicyclohexylcarbodiimide). The resulting mixture was stirred at 0° C. for one hour and then at room temperature for 18 hours. At the end of reaction, 10 ml of 5% acetic acid was added, the solvent was distilled off under reduced pressure, the residue was extracted with ethyl acetate, and the extract was washed with 0.1% acetic acid, water and saturated aqueous solution of sodium chloride in that order, giving 17 g of crude product. Purification of this crude product by silica gel chromatography (chloroform:methanol=20:1) afforded 3.5 g of pure product.

BOC-Pro-Hyp(OBzl)-Gly-Ala-Gly-OBzl $^1$H NMR (CDCl$_3$), δ: 1.40 (d, J=7 Hz, 3H), 1.43 (s, 9H), 1.6-2.7 (m, 6H), 3.2-4.8 (m, 12H), 4.52 (s, 2H), 5.12 (s, 2H), 7.1-7.8 (m, 13H).

IR, $\nu_{max}^{KBr}$: 3310, 1752, 1670 cm$^{-1}$.

(5) Preparation of N-3-(4-benzyloxyphenyl)propionyl-L-prolyl-O-benzyl-L-hydroxyprolyl-glycyl-L-alanyl-glycine benzyl ester L-Prolyl-L-hydroxyprolyl-glycyl-L-alanyl-glycine benzyl ester hydrochloride (1.81 g) (prepared in the synthesis of L-prolyl-L-hydroxyprolyl-glycyl-L-alanyl-glycine benzyl ester) was suspended in dichloromethane, the suspension was cooled to 0° C., triethylamine (0.42 ml), 3-(4-benzyloxyphenyl)propionic acid (*1) (1.12 g) and dicyclohexylcarbodiimide (0.90 g) were added to the suspension, and the mixture was stirred at 0° C. for 90 minutes. The reaction mixture was filtered, the filtrate was concentrated, and the crude product thus obtained (3.7 g) was purified by silica gel chromatography (chloroform:methanol=20:1), giving 1.77 g of pure product.

$^1$H NMR (CDCl$_3$), δ: 1.41 (d, J=7 Hz, 3H), 1.7-4.2 (m, 19H), 4.2-4.7 (m, 3H), 4.45 (s, 2H), 4.95 (s, 2H), 5.06 (s, 2H), 6.77 (d, J=9 Hz, 2H), 7.08 (d, J=9 Hz, 2H), 7.1-7.8 (m, 18H).

IR, $\nu_{max}^{KBr}$: 3310, 1750, 1650 (bs)cm$^{-1}$.

(*1) Preparation of 3-(4-benzyloxyphenyl)propionic acid:

(1) 3-(4-Hydroxyphenyl)propionic acid (5 g), potassium carbonate (16 g) and tetrahydrofuran (50 ml) were placed in a three-necked flask, 8.5 ml of benzyl bromide was added dropwise through a syringe under stirring, and the mixture was heated under reflux overnight. After filtering off the solid matters, the solvent was distilled off, and the residue was purified by column chromatography on silica gel (50 g), affording 9.25 g (89.3%) of pure benzyl 3-(4-benzyloxyphenyl)propionate.

(2) Benzyl 3-(4-benzyloxyphenyl)propionate (9.25 g) and a solution of 2.8 g potassium hydroxide in 95% ethanol (125 ml) were placed in a flask, and the mixture was heated under reflux for 30 minutes. At the end of reaction, the solvent was distilled off, ethyl acetate was added to the residue, and the resulting mixture was transferred to a separating funnel. After washing with 1N HCl and water, the ethyl acetate layer was collected and dried over anhydrous sodium sulfate, the solvent was distilled off from the dried solution, and the residue was recrystallized from ethyl acetate/hexane, affording 5 g (72.7%) of pure 3-(4-benzyloxyphenyl)propionic acid.

$^1$H NMR (CDCl$_3$), δ: 2.4–3.1 (m, 4H), 4.98 (s, 2H), 6.82 (d, J=9 Hz, 2H), 7.08 (d, J=9 Hz, 2H), 7.30 (s, 5H).

IR, $\nu_{max}^{KBr}$: 1690, 1612, 1582 cm$^{-1}$.

(6) Preparation of N-3-(4-hydroxyphenyl)propionyl-L-prolyl-L-hydroxyprolyl-glycyl-L-alanyl-glycine To a solution of N-3-(4-benzyloxyphenyl)propionyl-L-prolyl-O-benzyl-L-hydroxyprolyl-glycyl-L-alanyl-glycine benzyl ester (122 mg) in 5 ml methanol was added 61 mg of 10% palladium/carbon, and the mixture was stirred at room temperature for 90 minutes under normal pressure of hydrogen. At the end of reaction, the catalyst was filtered off, and the filtrate was concentrated, giving 69 mg of crude product. Purification by silica gel chromatography (chloroform:methanol=2:1) afforded 37 mg of pure product.

$^1$H NMR (MeOH-d$_4$+CDCl$_3$), δ: 1.40 (d, J=7 Hz, 3H), 1.6–2.4 (m, 6H), 2.4–3.1 (m, 4H), 3.2–4.8 (m, 11H), 6.62 (d, J=8 Hz, 2H), 6.94 (d, J=8 Hz, 2H).

IR, $\nu_{max}^{KBr}$: 3300, 1630 cm$^{-1}$.

EXAMPLE 2

Synthesis of

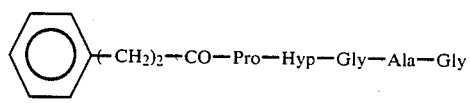 (i-a)

BOC-Gly (22 g) and triethylamine (17.5 ml) were dissolved in a mixture of ethanol (133 ml) and chloroform (67 ml), a resin (50 g) was put in this solution, and the mixture was stirred at room temperature for one hour and then heated under reflux at 90° C. for 48 hours. The resin thus treated was collected by filtration, washed with ethanol, acetic acid, water and methanol in that order, and dried at a temperature below 30° C. under reduced pressure. The BOC-Gly-Resin (55.7 g; 20.3 mmol Gly) thus obtained was placed in a solid-phase reactor (700 ml capacity), and amino-acid residues were successively introduced to the resin by repeating the cycle of protective-group removal, neutralization and coupling as shown below.

(1) Washing thrice with 350 ml of dichloromethane for three minutes; (2) releasing the protective groups by treating twice with 350 ml of 5% trifluoroacetic acid/dichloromethane (for three minutes and 20 minutes each); (3) washing eight times with 350 ml of dichloromethane for three minutes; (4) neutralization by treating twice with 350 ml of 10% triethylamine/dichloromethane for three minutes and ten minutes each; (5) washing five times with 350 ml of dichloromethane; (6) adding 60.8 mmol of BOC-amino-acid and 250 ml of dichloromethane and mixing for ten minutes; (7) adding 60.81 mmol of dicyclohexylcarbodiimide and 100 ml of dichloromethane and continuing reaction for two hours; and (8) washing five times with 350 ml of dichloromethane.

BOC-Ala, BOC-Gly, BOC-Hyp(OBzl), BOC-Pro and 3-phenylpropionic acid were introduced by repeating the cycle of operations described above, and the resulting resin was vacuum-dried at a temperature below 30° C. The dry resin was placed in an HF-reactor, anisole (10 ml) and anhydrous hydrofluoric acid (100 ml) were added, and the reaction was carried out at 0° C. for one hour. Excess hydrofluoric acid was distilled off, the residue was thoroughly washed with methanol, the resin was filtered off, and the filtrate was concentrated, leaving 8 g of oily product. Purification by silica gel column chromatography (chloroform:methanol=4:1) gave 4.3 g of pure product.

$^1$H NMR (MeOH-d$_4$+CDCl$_3$), δ: 1.41 (d, J=7 Hz, 3H), 1.5–2.4 (m, 6H), 2.5–3.1 (m, 4H), 3.2–4.7 (m, 11H), 6.8 (s, 5H).

IR, $\nu_{max}^{KBr}$: 3300, 1635 cm$^{-1}$.

EXAMPLE 3

Compound (ii) in Table 1 was prepared in the same manner as Example 1 except that N-3-(4-benzyloxyphenyl)propyl-L-proline N-hydroxysuccinimide ester was used in step (4).

EXAMPLE 4

Compound (ii-a) in Table 1 was prepared in the same manner as Example 2 except that N-3-phenylpropyl-L-proline was used in place of BOC-Pro.

TABLE 1

| Compound No. | R$_1$ | —Pro—Hyp—R$_2$ | IR |
|---|---|---|---|
| i (Example 1) | HO—⟨C$_6$H$_4$⟩—(CH$_2$)$_2$—CO— | —Pro—Hyp—Gly—Ala—Gly | 3300 (br) 1630 cm$^{-1}$ |
| i-a (Example 2) | ⟨C$_6$H$_5$⟩—(CH$_2$)$_2$—CO— | —Pro—Hyp—Gly—Ala—Gly | 3300 (br) 1635 cm$^{-1}$ |
| ii | HO—⟨C$_6$H$_4$⟩—(CH$_2$)$_2$—CH$_2$— | —Pro—Hyp—Gly—Ala—Gly | 3250 (br) 1615 cm$^{-1}$ |
| ii-a | ⟨C$_6$H$_5$⟩—(CH$_2$)$_2$—CH$_2$— | —Pro—Hyp—Gly—Ala—Gly | 3250 (br) 1620 cm$^{-1}$ |

TEST EXAMPLE 1

Platelet Agglutination Inhibitory Action

Blood samples were taken from the abdominal artery of rats by means of a syringe containing 3.8% solution of sodium citrate, and the mixture (sodium citrate:-blood=1:9) was centrifuged for ten minutes, giving platelet-rich plasma (PRP).

Figure 2:
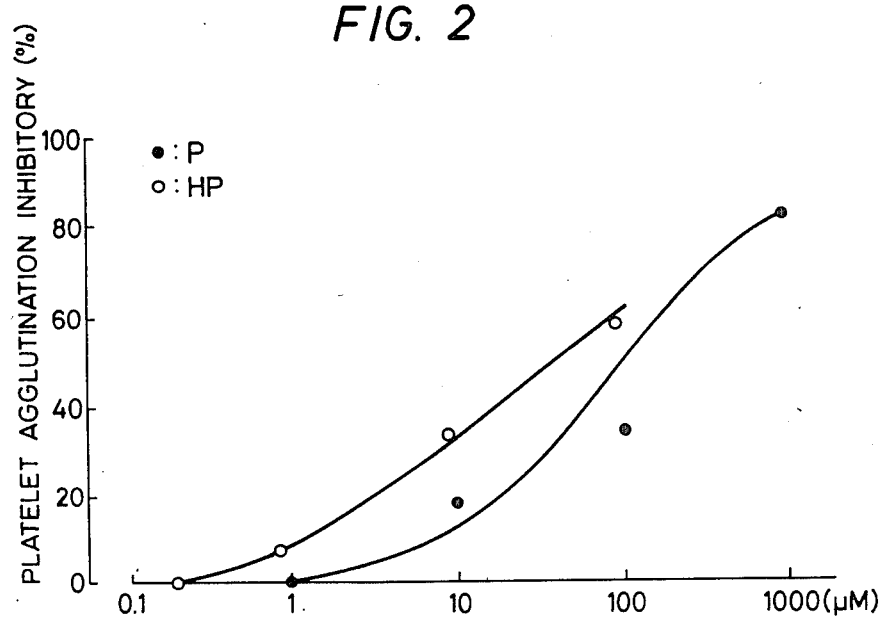
FIG. 2 also illustrates the in vitro inhibitory effects of compounds P and HP against thrombin-induced agglutination of rat PRP.
Figure 3:
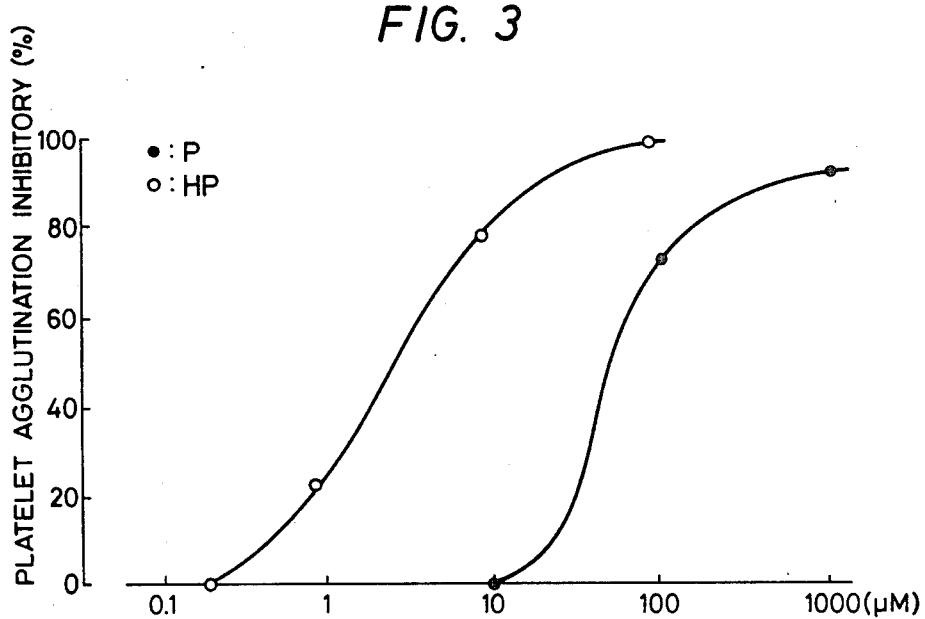
FIG. 3 further shows the in vitro inhibitory effects of compounds P and HP against agglutination of rat washed platelets induced by Ca ionophore A-23187.

PRP thus collected was placed in cuvettes and kept in an incubator held at 37° C. for two minutes. Solutions of the compound obtained in Example 1 with different concentrations (diluted with a solution of 1.5 mM EDTA in a mixture of Tris-HCl buffer and sodium chloride solution (1:5)) were added, the resulting mixture in each cuvette was incubated for three minutes, and Ca ionophore A-23187 (final concentration: 4 μM), arachidonic acid (1 mM) or thrombin (0.8 U/ml) was added to measure the degree of agglutination. A solution of heparin sodium was used in place of sodium citrate when arachidonic acid was employed as agglutination inducer. The result of test is summarized in FIGS. 1, 2, and 3. As can be seen from these FIGS., HP (the compound of this invention) showed about ten times stronger effects than compound P (control).

TEST EXAMPLE 2

Acute Toxicity

The compounds listed in Table 1 were orally, parenterally and intravenously administered to mice (three head for each group) at a dose of 1 g/kg. No mortality or abnormality was observed at all.

While the invention has been described in detail and with reference to specific embodiments thereof, it will be apparent to one skilled in the art that various changes and modifications can be made therein without departing from the spirit and scope thereof.

What is claimed is:

1. A peptide derivative represented by the following general formula

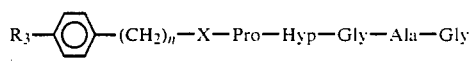

wherein X represents —CO—, —CH$_2$—, R$_3$ represents hydrogen or hydroxyl and n is an integer from 1 to 4.

2. The peptide derivative as claimed in claim 1, wherein n is 2.

3. The peptide derivative as claimed in claim 2, wherein X represents —CO— and R$_3$ represents hydroxyl.

4. The peptide derivative as claimed in claim 2, wherein X represents —CO— and R$_3$ represents hydrogen.

5. The peptide derivative as claimed in claim 2, wherein X represents —CH$_2$— and R$_3$ represents hydroxyl.

6. The peptide derivative as claimed in claim 2, wherein X represents —CH$_2$— and R$_3$ represents hydrogen.

7. The peptide derivative as claimed in claim 1, wherein X represents —CO— and R$_3$ represents hydroxyl.

* * * * *